United States Patent [19]

Sheldon et al.

[11] 4,386,602
[45] Jun. 7, 1983

[54] INTRACRANIAL SURGICAL OPERATIVE APPARATUS

[76] Inventors: Charles H. Sheldon, 1345 Bedford Rd., San Marino, Calif. 91108; Robert E. Frazer, 317 San Juan Way, La Canada, Calif. 91011; Harold R. Lutes, 556 Michigan Blvd., Pasadena, Calif. 91107

[21] Appl. No.: 797,843

[22] Filed: May 17, 1977

[51] Int. Cl.³ ............................................... A61B 1/00
[52] U.S. Cl. .................................. 128/4; 128/303 B; 128/341
[58] Field of Search ............... 128/303 B, 17, 4, 345, 128/343, 347, 2.1 E, 214.4, 341, 221, 2 B, 351, 5, 6, 7, 8

[56] References Cited

U.S. PATENT DOCUMENTS

| 3,169,529 | 2/1965 | Koenig | 128/345 X |
| 3,677,262 | 7/1972 | Zukowski | 128/351 X |
| 3,747,603 | 7/1973 | Adler | 128/341 |
| 3,994,557 | 11/1976 | Hopkins | 128/4 X |

FOREIGN PATENT DOCUMENTS

| 1242792 | 6/1967 | Fed. Rep. of Germany ... 128/303 B |
| 2115121 | 10/1972 | Fed. Rep. of Germany ... 128/303 B |

OTHER PUBLICATIONS

Amico illustrated catalog #26, p. 219, 1966.
National Publication, pp. 1 and 2, (1938).

Primary Examiner—Michael H. Thaler
Attorney, Agent, or Firm—Freilich, Hornbaker, Wasserman, Rosen & Fernandez

[57] ABSTRACT

Apparatus for operating on the brain with minimal disturbances thereto, including a bullet-shaped expandable device with an end that can be closed for insertion through a small hole in the brain. The device can be expanded after insertion to leave an air pocket through which to extend viewing and cutting devices which enable operation on tumors or the like that lie at the end of the expanded device. A set of probes of varying diameters are also provided, to progressively enlarge a passage leading to the tumor, prior to inserting the expandable device.

5 Claims, 7 Drawing Figures

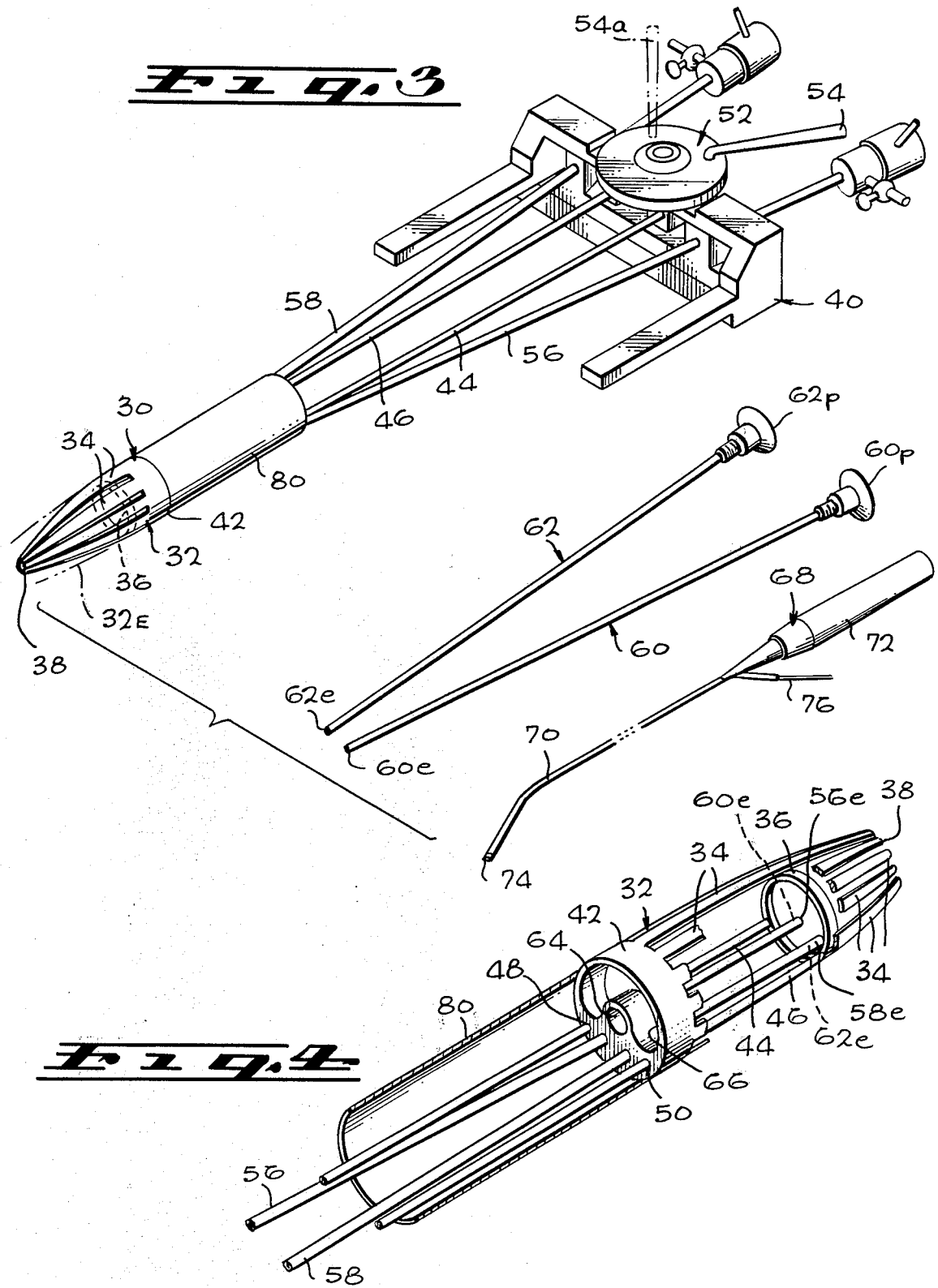

INTRACRANIAL SURGICAL OPERATIVE APPARATUS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

Recent developments in computerized tomography have enabled the location and diagnosis of brain lesions when they are extremely small. Prior art surgical methods for gaining access to the locations of large lesions, such as those over 3 centimeters in diameter, caused deleterious symptoms; however, those symptoms were typically minor compared to the symptoms caused by the lesion or the surgery performed thereon. The application of such techniques to enable access to presently-locatable lesions of a diameter of 5 millimeters or less, can produce symptoms of great magnitude compared to those resulting from just the removal or repair of the lesion.

Apparatus which enabled access to brain lesions, such as tumors, hematomas and aneurysms, to enable the viewing of the lesion through an endoscope or the like and to enable the application of surgical instruments to the lesion, all while causing minimal disruption of tissue leading to the lesion, would aid in performing more successful operations.

SUMMARY OF THE INVENTION

In accordance with one embodiment of the present invention, apparatus is provided which facilitates access to brain lesions with minimum disruption of tissue in the path leading to the lesion. The apparatus includes a tapered device for insertion into the brain so its tip is near the depth of the lesion, and means for expanding the tip portion to provide an air pocket through which the lesion can be viewed and through which surgical instruments can be inserted and manipulated. A set of probes also can be employed to enable gradual displacement of brain tissue lying over the lesion, to form a passageway through which the expandable device can be inserted.

The novel features of the invention are set forth with particularity in the appended claims. The invention will be best understood from the following description when read in conjunction with the accompanying drawings.

BRIEF DESCRIPTION OF THE DRAWINGS

FIG. 3 is a perspective view of an expander device and of apparatus which can be utilized therewith, all of which can be utilized with the apparatus of FIG. 1 to enable viewing and operating on a brain lesion;

FIG. 4 is a perspective, partially sectional view of the expander device of FIG. 3, showing the device in an expanded configuration;

DESCRIPTION OF THE PREFERRED EMBODIMENTS

Figure 1:
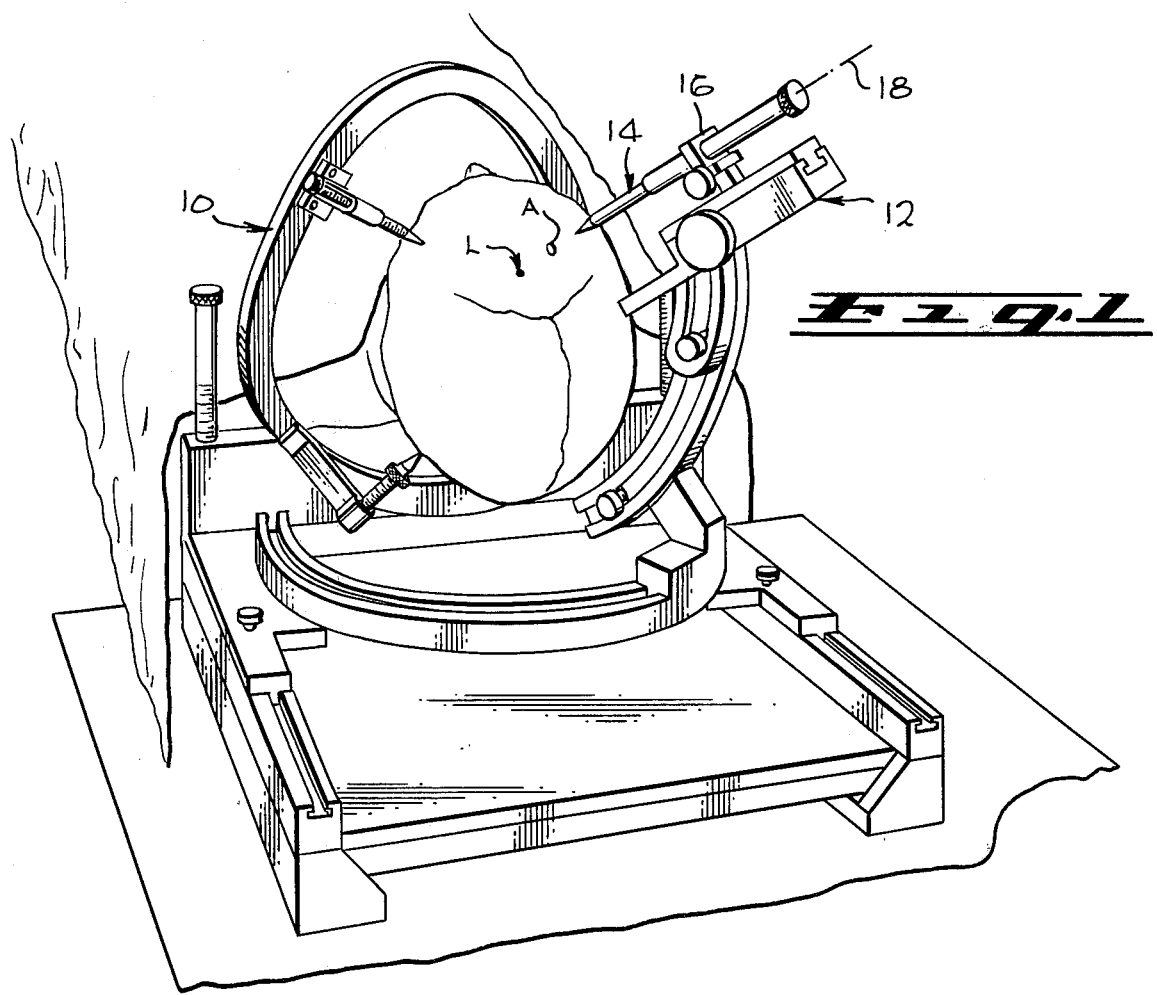
FIG. 1 is a perspective view of the apparatus of the invention, shown during an early stage of its utilization.

FIG. 1 illustrates an operatory system which includes a stereotaxic guide 10 for holding to the head of a patient, and a micromanipulator assembly 12 mounted on the guide to permit accurate manipulation of surgical instruments. The particular instrument shown in FIG. 1 is an expander probe 14 which is slidably mounted on a probe guide 16 to enable the probe to move along a predetermined axis 18 directed towards an aperture A that has been formed in the skull of a patient, and where the axis 18 is directed toward a lesion L lying under the aperture.

Figure 2:
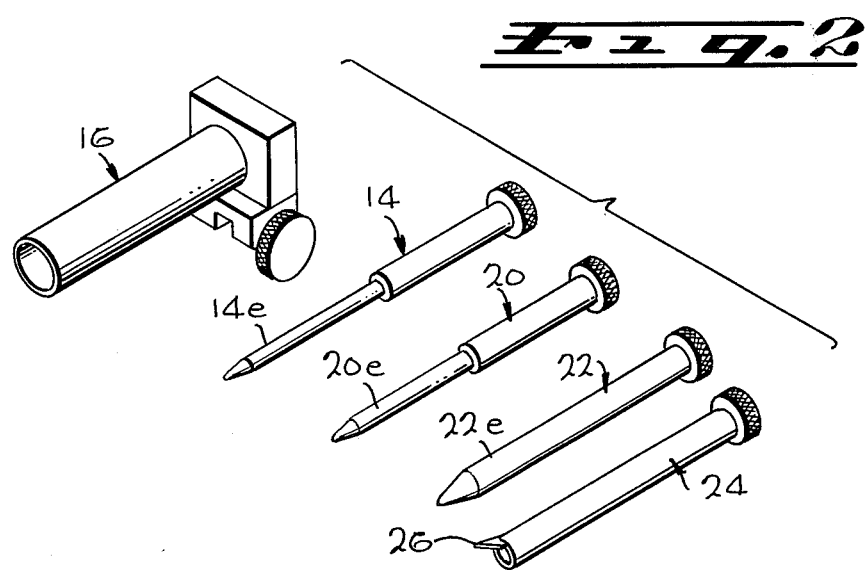
FIG. 2 is a perspective view of a probe and guide assembly which can be utilized with the apparatus of FIG. 1 to displace tissue so as to form a passageway leading to a brain lesion.

FIG. 2 shows details of the probe guide 16, and of additional instruments 20, 22, and 24 that can be slidably held by the probe guide. One instrument 24 includes a knife 26 that can be used to indicate where the aperture must be formed. After the aperture in the skull has been formed, the first probe 14, which has a small diameter outer end portion 14e, is inserted into the probe guide 16 and gently pressed forward into the brain to displace brain tissue about a narrow passageway leading to the lesion.

After a few minutes, the first probe is withdrawn and a second probe 20 with an outer end 20e of larger diameter than that of the first probe, is installed on the probe guide and slid into the passageway which has been formed in the brain tissue, to expand the passgeway. After a few minutes, the second probe is withdrawn and a third probe 22 having an outer end 22e of greater diameter than that of the second probe, is installed on the probe guide and gently pressed into the passageway formed in the brain tissue. When the last probe 22 has been withdrawn, an enlarged passageway has been formed leading to the lesion, to enable the insertion into that passageway of an expandable device 30 which is shown in FIG. 3.

The expandable device 30 includes a bullet-shaped, or tapered, body 32 with walls formed by eight tapered leaves 34. The leaves 34 can move together into a compacted configuration wherein the body 32 is substantially closed and has a tapered end for easy passage into tissue. The device also includes an expander 36 which can move the leaves 34 apart to expand the body into an expanded configuration 32e, wherein its end 38 is open. The expandable device is held on a mount 40 that can be attached to the micromanipulator assembly 12 of FIG. 1 to enable the movement of the bullet-shaped body 32 into the aperture of the patient's skull, along the same axis 18 where the probes were previously moved to form the passage into the brain tissue.

As also shown in FIG. 4, the expandable device 30 includes a frame comprising a collar 42 to which the leaves 34 of the expandable body are attached. The expandable body 32 can be formed from a hollow tapered member in which eight slits have been cut, so that the leaves are biased toward a compacted condition. The expander 36 is a ring-shaped member held by a pair of thin rods 44, 46 that are slidably received in a pair of holes 48, 50 of the collar 42. When the rods 44, 46 are slid forward towards the end 38 of the expandable body, the expander ring 36 causes the leaves of the body to bend apart, to move the device to an expanded configuration. The rods 44, 46 extend rearwardly to an expansion control mechanism 52 (FIG. 3) on the mount 40, to enable a surgeon to control expansion and contraction of the expandable device. When a handle 54 on the mechanism is turned to a position 54a, it causes the rods 44, 46 to be pulled back to allow the body to return to its compacted configuration.

The collar 42 of the expandable device is held by a pair of tubes 56, 58 to the mount 40. These tubes can receive the ends of two endoscopes 60, 62 (FIG. 3). The endoscopes are normally held with their objective ends 60e, 62e even with the outer ends of the tubes 56, 58. A physician peering through the eyepieces 60p, 62p of the endoscopes, whose outer ends are at the tube ends 56, 58, has a sterooptic view of tissue located at the tip 38 of the expandable body.

The collar 42 of the expandable device has a small hole 64 (FIG. 4) at its center, and has a large hole 66 along most of the collar portion which is not being otherwise utilized. An aspirated rotary dissector 68 (FIG. 3) is provided, which includes an angled tube 70, a handpiece 72 at one end of the tube for driving a shaft in the tube, and a small rotary cutter 74 contained within the distal end of the tube. A vacuum is applied through a flexible hose 76 and through the bent tube 70, to provide suction capability to draw out material dislodged by the cutter 74. The bent tube 70 can fit through the collar 42 of the expandable device, either through the small hole 64 to facilitate positioning of the cutter, or through the large hole 66 to facilitate movement of the cutter. It may be noted that the expandable device includes a tube-like guard 80 extending rearwardly from the collar 42 to enable the insertion of the expandable device deep into tissue, while minimizing disturbance of all tissue through which the device extends.

Figure 5:
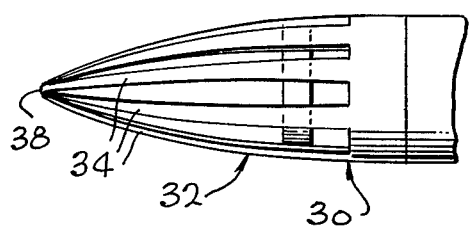
FIG. 5 is a side elevation view of the expander device of FIG. 1, shown in a closed configuration.
Figure 6:
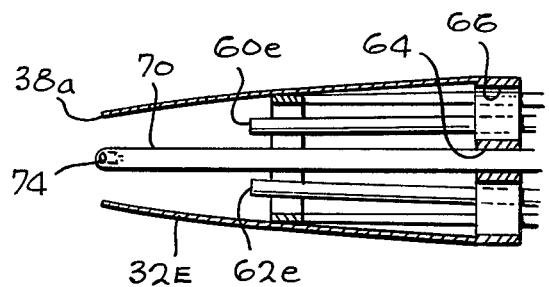
FIG. 6 is a sectional side view of the expander device of FIG. 5, shown in an expanded configuration.
Figure 7:
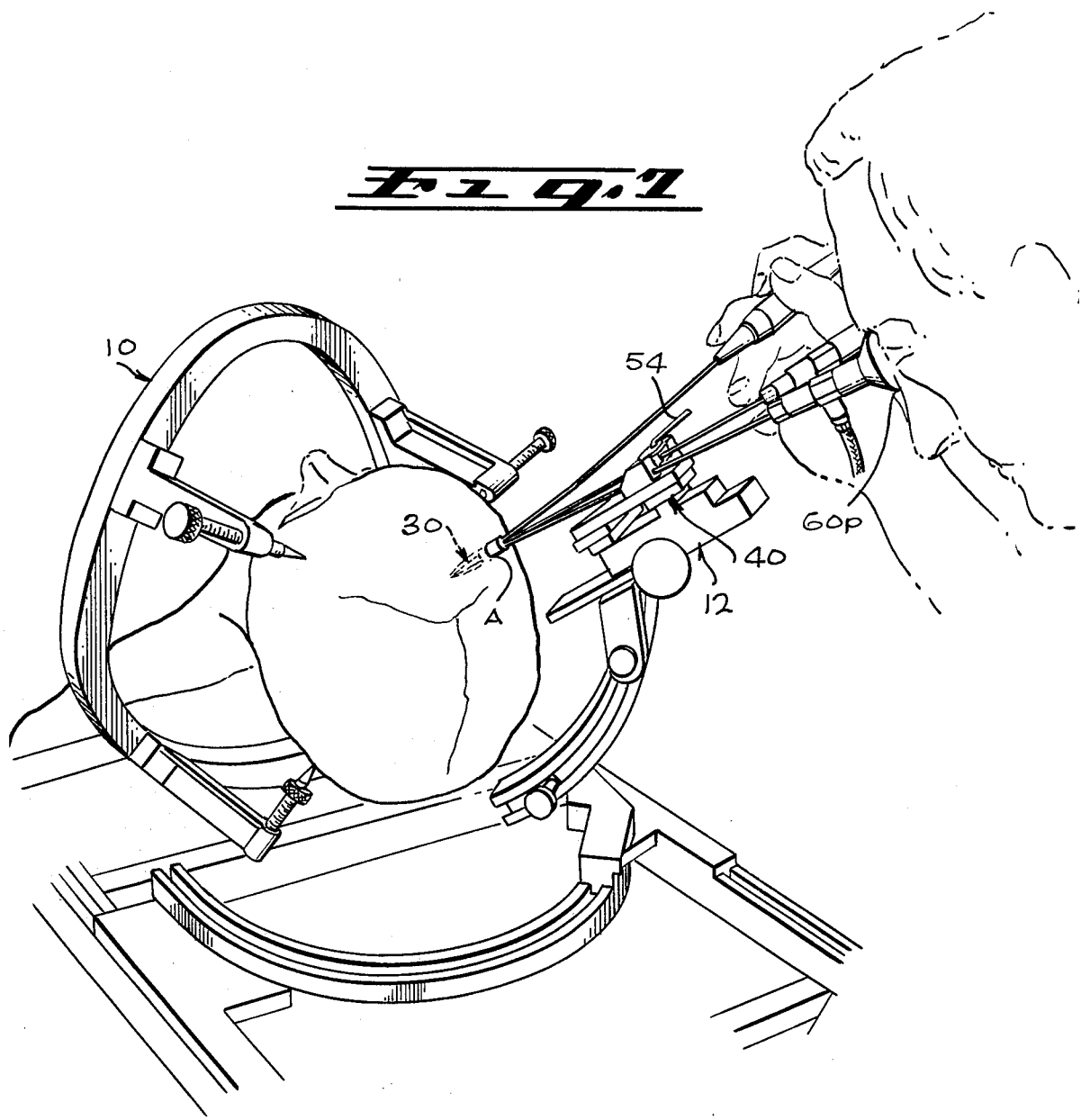
FIG. 7 is a perspective view of the apparatus of FIG. 1, but shown during utilization of the expander device and associated apparatus of FIG. 3.

FIG. 7 illustrates the expandable device 30 extending through the aperture in the patient, with the mount 40 which holds the expandable device being held on the same micromanipulator 12 as was used to insert the series of probes. FIG. 5 illustrates the expandable device 30 in a compacted configuration to enable insertion through a passageway leading through brain tissue. FIG. 6 illustrates the expandable device with the body 32e expanded to open its end. The ends 60e, 62e of the endoscopes are then at a distance from the extreme end of the open body so that tissue located thereat is in focus when viewed through the endoscopes. The opening also permits the projection of the rotary extractor tube 70 so that the cutter 74 can cut away a tumor located at the bottom of the passageway. When aneurysms are to be operated upon, other surgical devices can be utilized which can be projected through the openings 64, 66 of the collar.

The expandable device 30 enables the insertion of the endoscopes and of surgical devices through a passageway formed in the brain, and manipulation of such instruments, with minimal disturbance of the tissue around this passageway.

At the time when the expandable device has been inserted and is then expanded to the configuration of FIG. 6, the expandable body can push away any tissue lying over the brain lesion to uncover the lesion and to form an air space through which to view the lesion. The collar of the expandable device serves to fix the location of the endoscopes so that a clear, unobstructed region is provided through which to insert and manipulate surgical instruments, all without repeatedly disturbing tissue along the passageway that leads to the lesion. The use of the probes 14, 20, 22, enables the gentle expansion of tissue to form the passageway leading to the lesion. The fact that the probes all can be inserted along a common axis and that the expandable device also can be inserted along the same axis, further aids in minimizing disturbance to surrounding tissue. In one apparatus, the probe ends 14e, 20e, and 22e had outside diameters of 6 mm, 11 mm and 16 mm, respectively, while the expander body had a maximum outside diameter of 16 mm.

The operatory apparatus of this invention is useful for operating on rigid portions of the body, particularly the head and sometimes also the neck. When operating on a tumor, the location of the tumor, and the fact that it is not a blood clot, can be verified by administering a drug that it is known will be absorbed selectively by the tumor, and wherein the drug has been tagged with a radioisotope. Then, the operatory apparatus can be utilized to insert a probe with an outside shape similar to probe 14, but which contains a radioisotope detector at its tip. The detection of the radioisotope will confirm that the lesion is a tumor.

When operating on an aneurysm, the operatory apparatus can be utilized to accurately guide a clamp-holding device, to assure that the clamp is accurately applied. In this connection, a mechanism can be employed to enable remote closing of the clamp after it has been positioned by remote control.

The location of lesions is often accomplished by the use of computerized axial tomography, which provides precise coordinates of the location of the lesion. These coordinates can be used to set up the stereotaxic equipment, so that the probes will move directly to the lesion.

The novel features of the invention are set forth with particularity in the appended claims. The invention will be best understood from the following description when read in conjunction with the accompanying drawings.

What is claimed is:

1. Intracranial surgery operative apparatus comprising:

a probe guide;

a plurality of probes alternately slidable on said probe guide along the same axis, each of said probes having a substantially cylindrical outer portion with a tapered end, and different ones of said probes having outer portions of different diameters;

an expander which has a frame and an expandable body on said frame, said expandable body having walls and having means for holding said walls in a first configuration wherein said walls of said device form a tapered member with a substantially closed end and in a second configuration wherein the walls form a substantially open end; and means mountable to the head of a patient, for holding said probe guide and for subsequently supporting said expander so it can move along the same axis as said probes.

2. Intracranial surgical operative apparatus, comprising:

a frame;

an expander device mounted at an end of said frame, said expander device having walls at an end portion thereof and having means for deploying said walls between a compacted configuration wherein said walls form a tapered member with a substantially closed narrow end, and an expanded configuration wherein said walls form an open end;
a probe having an outer end portion of smaller outside diameter than the compacted expander device, and having a tapered outer end, said probe having an inner end; and
means mountable to the head of a patient for slidably guiding said probe and said frame alternately along the same predetermined axis with respect to the patient's head.

3. Surgical operative apparatus, comprising:

a frame;

a plurality of leaves having inner ends mounted on said frame and outer ends that can move together and apart to respectively form a largely closed and open end;

means for moving said leaves, including an annular member slidable within said leaves to force them apart, and a pair of rods connected to said annular member to move it; and a collar mounted to said frame and forming a first pair of holes slidably receiving said rods, and forming a second hole for guiding a surgical instrument.

4. Surgical operative apparatus, comprising:

a frame;

a plurality of leaves having inner ends mounted on said frame and outer ends that can move together and apart to respectively form a largely closed and open end;

means for moving said leaves, including an annular member slidable within said leaves to force them apart, and at least one elongated member mounted to said annular member to move it;

a collar mounted to said frame and forming a first hole slidably guiding said elongated member, and forming a second hole for guiding a surgical instrument; and a pair of microscopes having a pair of eyepieces and a pair of objective ends, said microscopes each having objective end portions mounted on said collar, with said eyepieces far behind said leaves and with said objective ends located at a distance behind the tips of said leaves at which an object immediately in front of said leaf tips is in focus and in the field of view of both microscopes.

5. Surgical operative apparatus, comprising:

a frame;

a plurality of leaves having inner ends mounted on said frame and outer ends that can move together and apart to respectively form a largely closed and open end;

means for moving said leaves, including an annular member slidable within said leaves to force them apart, and at least one elongated member mounted to said annular member to move it;

a collar mounted to said frame and forming a first hole slidably guiding said elongated member; and at least one microscope having an eyepiece and an objective end, said microscope having an objective end portion mounted on said collar, with said eyepiece far behind said leaves and with said objective end located at a distance behind the tips of said leaves at which an object immediately in front of said leaf tips is in focus and in the field of view of said microscope.

* * * * *